United States Patent
Burkhart et al.

(10) Patent No.: US 6,641,597 B2
(45) Date of Patent: Nov. 4, 2003

(54) INTERFERENCE FIT KNOTLESS SUTURE ANCHOR FIXATION

(75) Inventors: Stephen S. Burkhart, San Antonio, TX (US); R. Donald Grafton, Naples, FL (US); Peter J. Dreyfuss, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 10/153,927

(22) Filed: May 24, 2002

(65) Prior Publication Data

US 2003/0004545 A1 Jan. 2, 2003

Related U.S. Application Data

(60) Provisional application No. 60/350,020, filed on Jan. 23, 2002, and provisional application No. 60/293,170, filed on May 25, 2001.

(51) Int. Cl.⁷ .............................................. A61B 17/04
(52) U.S. Cl. ...................................... 606/232; 606/148
(58) Field of Search .......................... 606/72, 73, 74, 606/232, 113, 144, 148

(56) References Cited

U.S. PATENT DOCUMENTS

| | | | | | |
|---|---|---|---|---|---|
| 5,100,417 A | * | 3/1992 | Cerier et al. | ................ | 606/139 |
| 5,224,946 A | * | 7/1993 | Hayhurst et al. | ............. | 606/72 |
| 5,782,864 A | * | 7/1998 | Lizardi | ........................ | 606/232 |
| 5,964,783 A | * | 10/1999 | Grafton et al. | ............. | 606/232 |
| 5,980,558 A | * | 11/1999 | Wiley | ......................... | 606/232 |
| 2002/0013608 A1 | | 1/2002 | ElAttrache et al. | | |

* cited by examiner

*Primary Examiner*—Gary Jackson
(74) *Attorney, Agent, or Firm*—Dickstein Shapiro Morin & Oshinsky, LLP

(57) ABSTRACT

A suture anchor includes a body having a distal end and a proximal end. Projections in the form of ribs or threads are formed on the body for retaining the anchor in a hole formed in bone. An eyelet formed on the distal end of the body accepts suture. The eyelet preferably is formed by a loop of suture. Where the body of the anchor is formed of a polymer, the suture loop can be formed by insert-molding the suture into the body. Tissue is reattached to bone using the suture anchor by securing a length of suture to the tissue, and threading the length of suture through the eyelet on the distal end of the anchor, leaving lengths of suture extending from either side of the eyelet. Installing the suture anchor into the bone wedges the lengths of suture between the suture anchor and the bone, thereby securing the tissue without the need for tying knots. Pullout strength can be enhanced by twisting the lengths of suture prior to installation of the anchor into the bone.

14 Claims, 3 Drawing Sheets

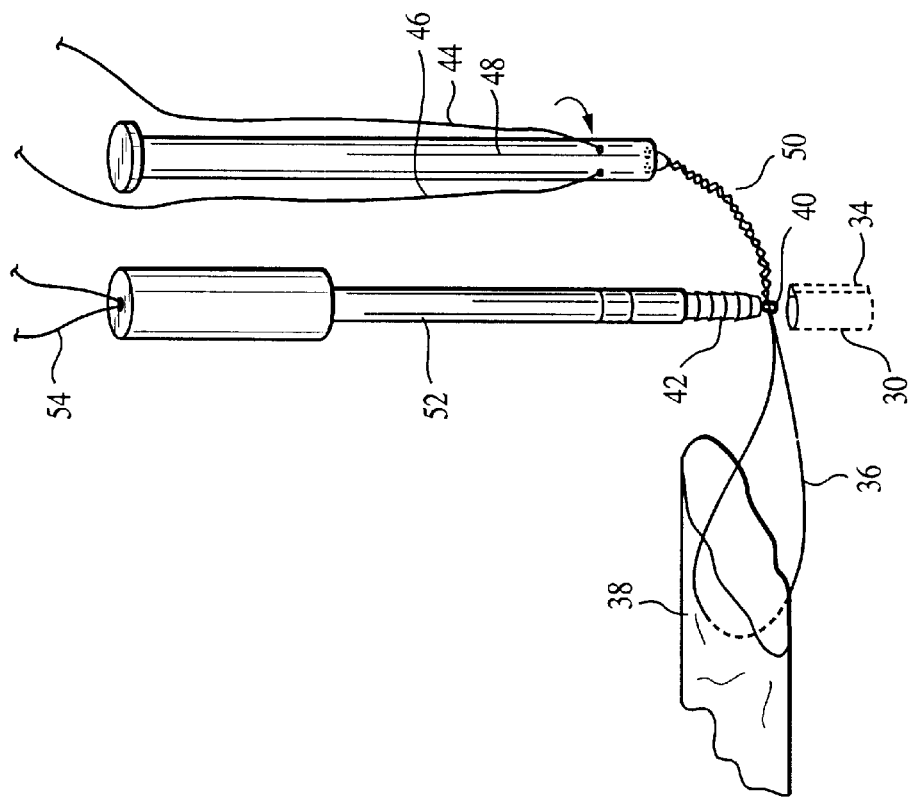
FIG. 7
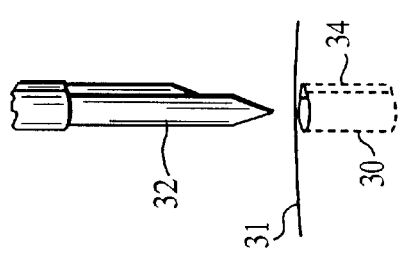
FIG. 6
FIG. 8

INTERFERENCE FIT KNOTLESS SUTURE ANCHOR FIXATION

This application claims the benefit of U.S. Provisional Application Serial No. 60/293,170, filed May 25, 2001, and U.S. Provisional Application Serial No. 60/350,020 filed Jan. 23, 2002.

BACKGROUND OF THE INVENTION

1. Field of the Invention

The present invention relates to devices and methods for securing soft tissue to bone, and more particularly, to suture anchors for proximating tissue to bone using knotless interference fixation.

2. Related Art

When soft tissue such as a ligament or a tendon becomes detached from a bone, surgery may be indicated to reattach or reconstruct the tissue. Various fixation devices, including sutures, screws, staples, wedges, and plugs have been used in the past to secure soft tissue to bone.

More recently, various types of suture anchors have been developed. The suture anchors are implanted in bone, and suture passed through the soft tissue is secured to the suture anchor. The technique usually requires the surgeon to tie knots in the suture, which is tedious and time-consuming, particularly in an arthroscopic procedure. Surgical procedures would be less cumbersome for the surgeon and ultimately more beneficial to the patient if the tissue could be attached to the bone without the surgeon having to tie suture knots.

U.S. Patent Publication No. 2002/0013608 A1, dated Jan. 31, 2002, of common assignment with the present application and incorporated herein by reference, discloses a method of graft fixation using an interference screw. Suture is attached to the graft and inserted into a pre-drilled hole. The interference screw is driven into the pre-drilled hole to secure the suture. The procedure would be simpler if the tissue could be transported toward the suture anchor more directly, and the step of inserting the suture into the pre-drilled hole could be eliminated. Enhancement of the pull-out strength of the construct also is desirable.

Insert molded suture anchors are disclosed in U.S. Pat. No. 5,964,783 issued on Oct. 12, 1999 to Grafton et al., of common assignment with this application and incorporated in its entirety herein by reference.

SUMMARY OF THE INVENTION

The present invention provides a suture anchor construct that does not require knots. The construct includes a ribbed or threaded suture anchor having a suture eyelet provided on a distal end of the anchor. Lengths of repair suture that have been passed through soft tissue are threaded through the eyelet and inserted simultaneously with the anchor into a preformed hole. Advantageously, a flexible eyelet can be formed in a polymeric suture anchor by insert-molding a looped length of suture within the suture anchor such that a closed portion of the suture loop extends from the distal end of the anchor.

The anchor of the present invention is used for tissue repair involving reattachment of soft tissue to bone. A hole for the suture anchor is preformed in bone. Installing the anchor and suture into the bone hole opposes the tissue to the bone. The suture is held in the preformed hole by an interference fit. The interference fit is established by a wedge effect on the suture between the suture anchor and the walls of the bone socket.

Pull out strength of the construct can be increased by various methods. The interference fit can be enhanced, for example, by forming twists in the limbs of at least a portion of the suture that passes alongside the installed suture anchor body within the preformed hole. Twisting the suture increases a cable friction effect (friction between the twisted lengths of suture) and also increases the wedge effect. The wedge effect similarly will be enhanced by forming knots in the suture, or utilizing suture formed with irregular thicknesses. See FIG. 4 of U.S. Pat. No. 5,964,783, for example.

Other features and advantages of the present invention will become apparent from the following description of the invention which refers to the accompanying drawings.

BRIEF DESCRIPTION OF THE DRAWINGS

FIG. 6 diagrams a step of forming a keyway with a punch according to an alternative method of repairing tissue according to the present invention.

FIG. 7 illustrates further steps of an alternative method of repairing tissue according to the present invention.

FIG. 8 illustrates a repair construct completed using the alternative method of repairing tissue according to the present invention.

DETAILED DESCRIPTION OF EMBODIMENTS OF THE INVENTION

Figure 1:
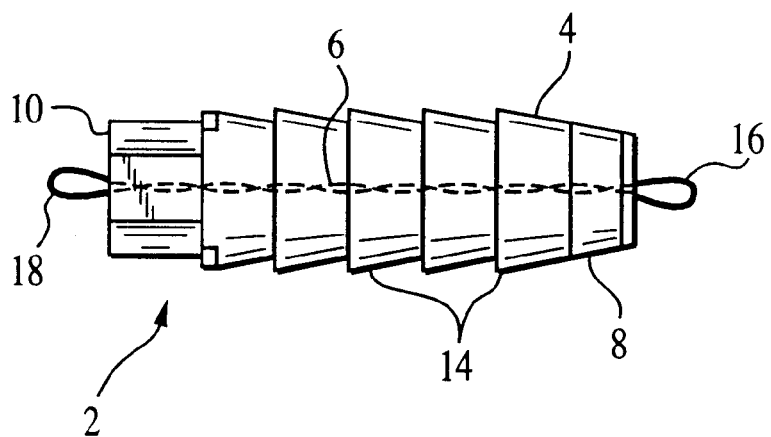
FIG. 1 is a plan view of a ribbed suture anchor having a distal suture loop eyelet according to the present invention.

Referring to FIG. 1, a suture anchor 2 according to the present invention is shown. Suture anchor 2 includes an anchor body 4 and a section of suture 6 forming a loop inside the suture anchor body. Anchor body 4 has a tapered distal end 8 and a proximal end with a drive head 10 formed to complement a suture anchor driver 12, shown schematically in FIG. 4. The anchor body 4 is provided with multiple, circumferential ribs 14 to enhance pull-out strength of the anchor from bone.

Suture section 6 is formed into distal loop 16 and an optional additional proximal loop 18 by overlapping or abutting two ends of the suture 6 and insert molding the suture while forming anchor body 4. The overlapping ends of suture can be twisted around each other or provided with knots, for example, to enhance pull-out strength of the suture from the anchor body.

Figure 2:
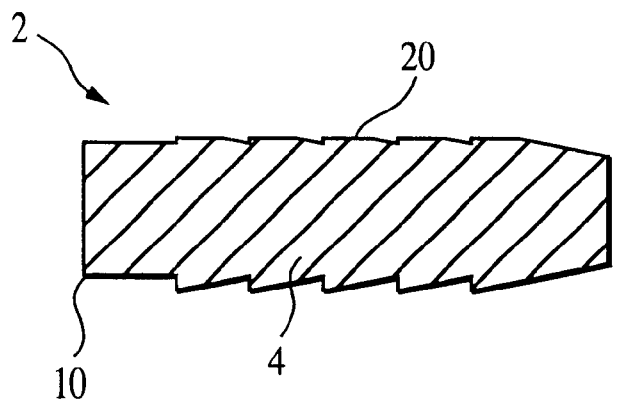
FIG. 2 is a cross-sectional side view of the suture anchor of FIG. 1.
Figure 3:
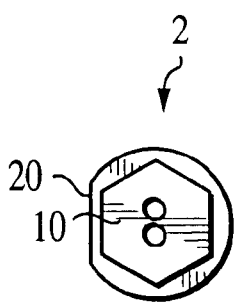
FIG. 3 is an end view of the suture anchor of FIG. 1 showing the hexagonal drive head.

Referring to FIG. 2, a flat 20 optionally can be formed on one side of the anchor body to provide a clearance for tissue suture passing back along the side of the anchor, as described in more detail below. Referring to FIG. 3, drive head 10 is provided in a complementary hexagonal configuration to engage driver 12.

Figure 4:
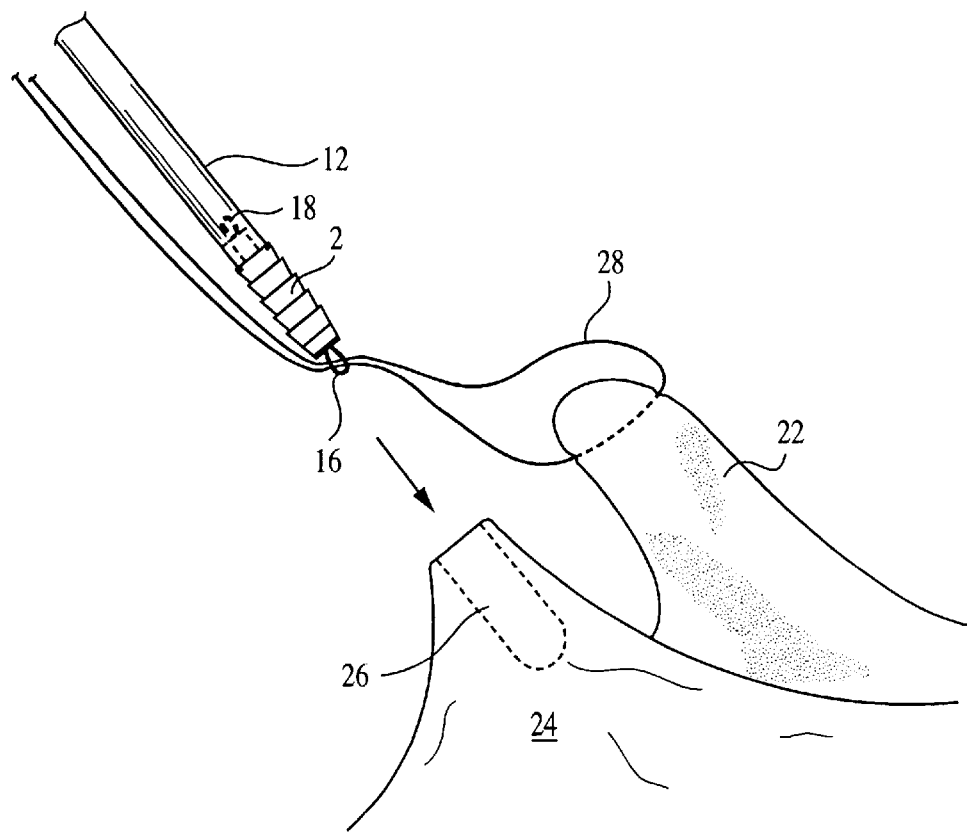
FIG. 4 is a schematic drawing of a step in a method of repairing tissue using a suture anchor according to the present invention.
Figure 5:
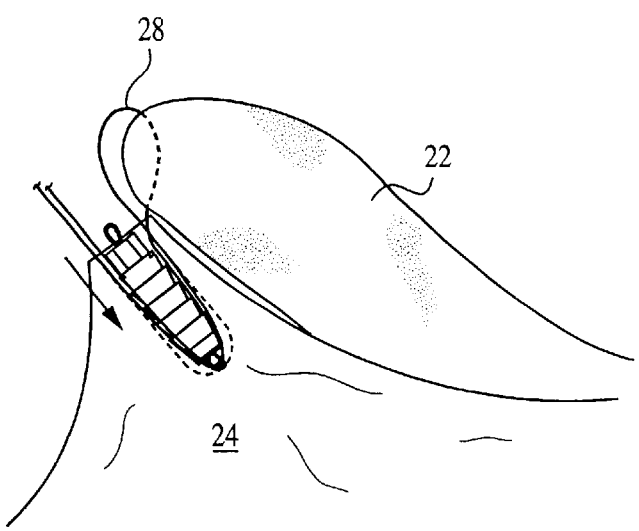
FIG. 5 is a schematic drawing of another step in the method of repairing tissue using a suture anchor according to the present invention.

Referring to FIGS. 4 and 5, a method of attaching tissue 22 to bone 24 is shown schematically. A hole 26 is preformed in bone 24, such as the glenoid rim. A length of suture 28 is inserted through tissue 22 and through distal loop 16 of anchor 2. Driver 12 engages drive head 10. Driver 12 is cannulated at least partially to accommodate proximal suture loop 18.

As shown in FIG. 5, suture anchor 2 is driven into hole 26, drawing tissue suture 28 in to oppose tissue 22 to the bone surface adjacent the opening of bone hole 26. Prior to driving the suture, the tissue has been pulled toward the tissue anchor, preferably to a distance approximately one anchor length from the tip of the anchor. The tissue suture passes back out of the hole by way of the relief provided by flat 20 on the side of anchor body 4. Alternatively, an anchor without a flat can be provided for stronger interference fixation as a result of the tissue suture being wedged more firmly between the wall of the bone hole and the body of the anchor. Proximal suture loop 18 remains proud for further suturing needs.

Referring to FIGS. 6–8, alternative steps in the method of attaching tissue are illustrated. A hole 30 is pre-formed in bone 31, as shown in FIG. 6. Hole 30 is produced with a keyway punch 32 to form offset channel 34 which accommodates a nest of twisted suture, as described further below.

Referring to FIG. 7, a length of suture 36 is inserted or looped through tissue 38 and through distal loop 40 of anchor 42. Anchor 42 optionally can differ from anchor 2 described above by having, for example, only a single, distal eyelet 40. Legs 44 and 46 of suture 36 are twisted together either by hand or by threading the legs into spinning a twisting tool 48 having diagonal openings in which suture legs 44, 46 are received. Twisting the suture legs creates a suture "nest" 50 which is received in channel 34 and becomes wedged by anchor 42.

Driver 52 is impacted to install anchor 42 such that nest 46 is received in offset channel 34. As suture anchor 42 is driven into hole 30, suture 36 draws tissue 38 toward bone hole 30, the length of suture 36 remaining between eyelet 40 and edge of tissue 38 having been adjusted to equal the length of anchor 42 prior to insertion. Suture twisting tool 44 may be combined with the driver.

Anchor 42 is shown fully seated in FIG. 8, with suture nest 50 installed in channel 34 formed away from tissue 38. Alternatively, suture nest 50 can be in a channel formed adjacent the tissue. According to a further alternative method step, suture nest 50 can be formed by twisting the anchor, rather than twising the suture with a separate tool. Traction suture 54 optionally can be attached to anchor 42 to hold the anchor on the end of driver 52. As a further option, the anchor can be threaded, and installed by rotating the anchor with the suture through the distal eyelet.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A suture anchor comprising:
   a body having a distal end and a proximal end;
   projections formed on the body for retaining the anchor in a hole formed in bone;
   a drive head formed on the proximal end of the body; and
   an eyelet formed on the distal end of the body.

2. The suture anchor of claim 1, wherein the body is cylindrical.

3. The suture anchor of claim 1, wherein the projections are selected from the group consisting of ribs and threads.

4. The suture anchor of claim 1, wherein the eyelet is formed by a loop of suture.

5. The suture anchor of claim 4, wherein the body is formed of a polymer, and the loop of suture is insert molded in the body.

6. The suture anchor of claim 5, further comprising an eyelet formed on the proximal end of the body.

7. A method of reattaching tissue to bone using a suture anchor having an eyelet formed on a distal end of the anchor and a drive head formed on a proximal end of the anchor, the method comprising the steps of:
   securing a length of suture to tissue;
   threading the length of suture through the eyelet on the distal end of the anchor, leaving lengths of suture extending from either side of the eyelet; and
   installing the suture anchor into the bone, whereby the lengths of suture are wedged between the suture anchor and the bone.

8. The method of claim 7, further comprising the step of forming twists in the length of suture such that the twists are wedged between the installed suture anchor and the bone.

9. The method of claim 8, wherein the twists are formed by rotating the suture.

10. The method of claim 7, further comprising the step of creating an opening in the bone for receiving the suture anchor.

11. The method of claim 7, wherein the opening in the bone is a socket formed in a keyhole shape.

12. The method of claim 7, wherein the anchor is ribbed, and the installation step includes impaction of the anchor.

13. The method of claim 7, wherein the anchor is threaded, and the installation step includes rotation of the anchor.

14. The method of claim 7, wherein the anchor has a length, and a length of suture left between the anchor eyelet and the tissue is equal to the length of the anchor.

* * * * *